US010168305B2

(12) United States Patent
Pirkle et al.

(10) Patent No.: US 10,168,305 B2
(45) Date of Patent: Jan. 1, 2019

(54) CONTAINER SCREENING SYSTEM AND METHOD

(71) Applicants: Wesley C. Pirkle, New Albany, OH (US); Richard L. Shoaf, Westerville, OH (US)

(72) Inventors: Wesley C. Pirkle, New Albany, OH (US); Richard L. Shoaf, Westerville, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 861 days.

(21) Appl. No.: 14/517,686

(22) Filed: Oct. 17, 2014

(65) Prior Publication Data
US 2015/0107361 A1    Apr. 23, 2015

Related U.S. Application Data

(60) Provisional application No. 61/892,138, filed on Oct. 17, 2013.

(51) Int. Cl.
*G01N 29/36*    (2006.01)
*G01N 29/44*    (2006.01)
*G01N 29/02*    (2006.01)

(52) U.S. Cl.
CPC .......... *G01N 29/44* (2013.01); *G01N 29/02* (2013.01); *G01N 2291/044* (2013.01); *G01N 2291/048* (2013.01); *G01N 2291/102* (2013.01)

(58) Field of Classification Search
CPC .. G01N 29/44; G01N 29/02; G01N 2291/048; G01N 2291/102; G01N 2291/044
See application file for complete search history.

(56) References Cited

U.S. PATENT DOCUMENTS

| | | | | |
|---|---|---|---|---|
| 2012/0055253 A1* | 3/2012 | Sinha | ................... | G01N 29/024 73/622 |
| 2013/0265190 A1* | 10/2013 | Mukherjee | ............ | G01F 23/284 342/124 |
| 2014/0225614 A1* | 8/2014 | Prado | ................... | G01N 24/084 324/309 |
| 2014/0366626 A1* | 12/2014 | Kuroda | ................ | G21C 17/035 73/290 V |
| 2015/0060673 A1* | 3/2015 | Zimdars | .................. | G01S 17/88 250/341.2 |
| 2015/0276920 A1* | 10/2015 | Kim | ........................ | G01S 7/025 342/188 |

* cited by examiner

*Primary Examiner* — John Breene
*Assistant Examiner* — Mohammad Islam
(74) *Attorney, Agent, or Firm* — Benesch, Friedlander, Coplan & Aronoff LLP

(57) ABSTRACT

A system and method are disclosed for interrogating a liquid in a container. In one embodiment, methods are provided to interrogate and identify a container material type and a liquid within a container.

10 Claims, 17 Drawing Sheets

CONTAINER SCREENING SYSTEM AND METHOD

This application claims priority from U.S. Provisional Patent Application No. 61/892,138, filed on Oct. 17, 2013, which is incorporated by reference herein in its entirety.

BACKGROUND

The use of explosives has been a main component in the overall arsenal of terrorists. Particularly based on various terrorist events, such as the Madrid rail bombing, the London Underground attack and the more recent exposure of possible attacks on U.S. bound flights from overseas, there is a prevailing need for a unified approach to the detection of liquid explosives, particularly in the aviation industry, but also in other mass transit modes of transportation. More specifically, there exists a need for technology to detect and distinguish hazardous liquids such as, homemade explosives, acids, oxidizers, and flammable liquids from benign liquids, such as medical liquids, baby formula, beverages, lotions, hygiene products, contact lens solutions and the like.

Currently there exists a bottle screening unit that is commercially available. This device is a diagnostic instrument that employs radio frequency technology (RF) to analyze liquids in containers. The device can discriminate between certain threat and benign liquids in only a couple seconds. The device is lightweight and portable, being about the size of a laptop computer. The device is designed to be installed in high traffic locations, such as airports, stadiums, courthouses, subway stations and the like. The device relies exclusively on RF or microwave technology and techniques thought to be originally developed for use in ground-penetrating radar systems. Basically, the device assesses dielectric constants for liquids in opened and unopened glass and plastic containers.

FIG. 1 depicts a process and device schematic used to discriminate between threat and benign liquids. In general, this known sensing device 10 functions by having a transmitting antenna 15 emit a radio frequency pulse or sending signal 20 which is scattered by liquid 25 in a glass or plastic container 30. The scattered sending signal reflects back from liquid 25 as a receiving signal 35 and is picked up by signal receiving antenna 40. A signal generating block 45 activates transmitting antenna 15 while signal receiving antenna 40 sends receiving signal 35 for processing by a period adjusting block 50 and a processing unit 55 for performing a predetermined computation on averaged waveforms in predetermined time-based ranges, and calculating an effective dielectric constant for liquid 25 in container 30. A so-called impulse method includes using a repetitive electromagnetic wave with a rapidly changing waveform section and short duration time. The process starts at signal generating block 45 and then proceeds to signal transmitting antenna 15; signal receiving antenna 40; period adjusting block 40; processing unit 55 and finally to an output block (not shown).

Examples of received waveforms for gasoline 60 and water 70 are shown in FIGS. 2A and 2B. The differences in the two waveforms are clearly obvious to the human eye. The decision to indicate a safe liquid or a threat liquid is made by comparing a threshold value on the received RF signal. For liquids with high dielectric constants, the received signal will exceed the threshold, while the received signal for liquids with low dielectric constant will not exceed the threshold. A table of known dielectric constants is illustrated in FIG. 3. The ovals in FIG. 3 emphasize the substantial difference in dielectric constant values between the benign 80 and threat liquids 90.

As indicated above, this known sensing device 10 is designed to detect certain threat liquids in plastic and glass bottles. Glass bottles may range from clear to various colors and plastic bottles, depending on their processing and thermal history, may be either amorphous (transparent) or semi-crystalline (opaque and white). Plastic bottles can also exhibit a multiplicity of colors. Unfortunately, with known sensing device 10, container 30 must have a bottom thickness of no greater than 0.5 mm for plastic bottles and less than 1 cm for glass bottles, while the bottom of container 30 for either plastic or glass bottles must be greater than 5 cm in diameter. In addition, device 10, as designed, is currently limited to detecting low dielectric explosives and flammable liquids including gasoline, light oil, paint thinner, ethanol, isopropyl alcohol, toluene, cyclohexane, kerosene, benzene, lighter fuel, and similar compounds.

Sensing devices using only RF sensors cannot detect hazardous material in metal containers. Therefore, some known arrangements teach using ultrasonic testing to detect hazardous liquids. However, prior versions of ultrasonic sensing devices cannot easily determine proper placement of a container on a sensing tray in the sensing device or can only detect large containers meeting specific characteristics. Likewise, removal of the container is also not automatically detected. Some known versions of the sensing device rely on the operator to properly place the container and then initiate testing with the sensor, which can result in testing errors if the operator is not careful.

Furthermore, to make an accurate measurement, ultrasonic sensing devices must know the material used to make the container holding the sample. Ultrasonic sensing devices typically relied on an operator to input whether the container is made of plastic, glass, metal or cardboard. In most cases, the type of material forming the container is readily apparent; however, in some cases appearances may be misleading. Many tubes, such as those holding toothpaste appear to be made of plastic but are actually formed from painted foil. Also, certain juice containers have a foil liner that cannot be readily observed by the operator. Such containers may thus be misidentified by the operator which can compromise the accuracy of the scan results. There is a desire in the art to eliminate this source of error and identify the material in each container automatically.

Also, the accuracy of known devices requires improvement to avoid misclassification of an unknown liquid as harmless or hazardous. The current RF systems compare a measured dielectric constant of an unknown sample to those dielectric constant values, stored in a database, that correspond to known materials. However, only using dielectric constants is not considered accurate enough and is only effective at determining low dielectric liquids from high dielectric materials. Such devices cannot tell the difference between two low dielectric liquids or two high dielectric liquids. There exists a need in the art to identify unknown liquids with more accuracy.

The present application is directed to adding to the accuracy of known systems. Particularly desirable upgrade parameters include an ability to determine a presence of a container having been placed in a container screening system along with an ability to determine a type of materials forming a container. The present application is also directed to more accurately detecting hazardous materials stored in a wider range of container materials and from an expanded number of benign and hazardous liquids.

SUMMARY

In one embodiment, an apparatus for detecting if a sample is hazardous is provided, the apparatus comprising: a holder for supporting the sample; a radio frequency transmitter configured to send a signal to a position above the sensor pad so that a reflected signal waveform is produced; a radio frequency receiver configured to detect the reflected signal waveform; and a controller including a memory for storing a baseline reflected signal waveform, a comparison device configured to compare the reflected signal waveform and the baseline reflected signal waveform to determine if the sample is present and being supported by the holder and further configured to compare the reflected signal waveform and the baseline signal waveform to determine if the sample is hazardous.

In another embodiment, a method of detecting a presence of a sample in a screening system used to analyze contents of liquid-filled containers is provided, the method comprising: continuously monitoring a reflected signal waveform; conducting a discrete Fourier analysis on a baseline reflected waveform to convert the baseline reflected waveform into a transformed baseline waveform; continuously conducting a discrete Fourier analysis on the reflected waveform to convert the reflected waveform into a transformed reflected waveform; calculating a changing ratio of the transformed reflected waveform to the transformed baseline waveform; determining when the changing ratio passes a preset threshold indicating the presence of the sample; and comparing the reflected signal waveform and the baseline reflected signal waveform to determine if the sample is hazardous.

A method of detecting metal in a sample in a screening system used to analyze contents of liquid-filled containers is provided, the method comprising: detecting a reflected signal waveform; conducting a Fast Fourier Transformation of the reflected signal waveform to generate a signal transform; conducting a Fast Fourier Transformation of a baseline reflected signal to generate a baseline transform; calculating ratios of the signal transform to the baseline transform at different frequencies; and analyzing the reflected signal waveform to determine if the reflected signal waveform has a first peak saturation and a first minimum change that is greater than a preset voltage and by applying a partial least squares algorithm to the ratios to determine if PLS SubC<−0.05; and RS>0.75.

In another embodiment, a method for detecting if a liquid in a container is hazardous is provided, the method comprising the steps of: storing a baseline reflected signal; transmitting a radio frequency signal to the container to generate a reflected signal waveform as the radio frequency signal reflects off of the liquid in the container; detecting the reflected signal waveform; conducting a Fast Fourier Transformation of the reflected signal waveform to generate a signal transform; conducting a Fast Fourier Transformation of the baseline reflected signal to generate a baseline transform; calculating a ratio of the signal transform to the baseline transform; calculating a difference between the signal transform and the baseline transform; conducting a partial least squares regression analysis using the ratio and the difference to create a regression value for the sample; measuring an ultrasonic velocity of sound passing through the sample; measuring a temperature of the sample to compensate for changes in the radio frequency signal and ultrasonic velocity caused by temperature; calculating a signature of the liquid based on the regression value, the ultrasonic velocity, and the temperature; and comparing the signature of the liquid to a database of signatures of liquids to determine if the liquid is hazardous.

DETAILED DESCRIPTION

With reference to FIGS. 4-8, a screening system—that is, a combination of screening device 100 and base 160, may employ two measurement modalities to analyze contents of liquid-filled containers, which can be made from a wide range of materials including plastic, glass and metal materials, and discriminate between hazardous and benign (non-hazardous) liquids. In one embodiment, a screening system is utilized in at an airport security inspection point, although a screening system could certainly be used in any public or private environment. In any embodiment, a first modality of a screening system may be ultrasonic/acoustic interrogation, while a second modality may be radio frequency (RF) interrogation.

Mechanical Design

Figure 1:
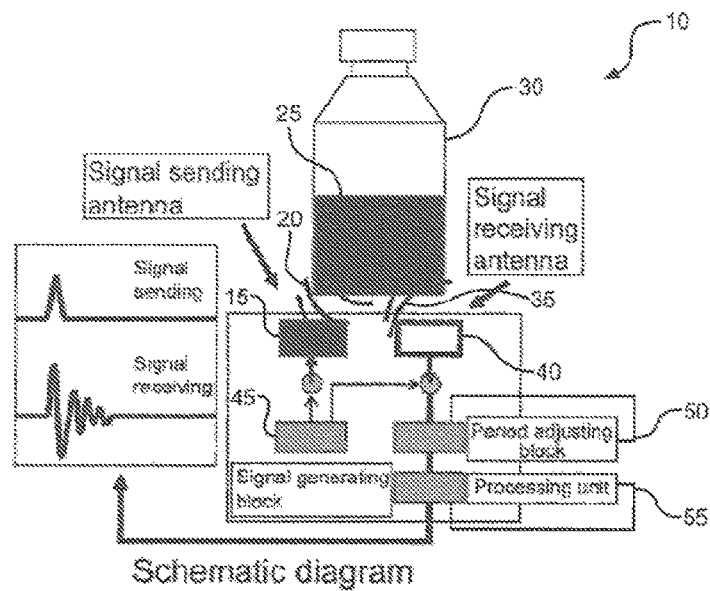
FIG. 1 illustrates a schematic of an example device used to discriminate between threat and benign liquids.
Figure 2A:
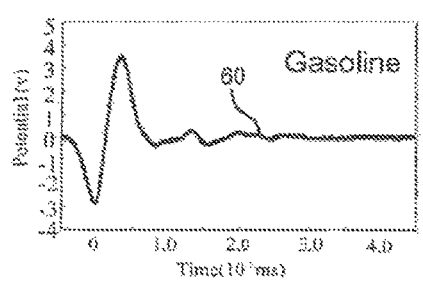
FIG. 2A illustrates known waveforms for gasoline.
Figure 2B:
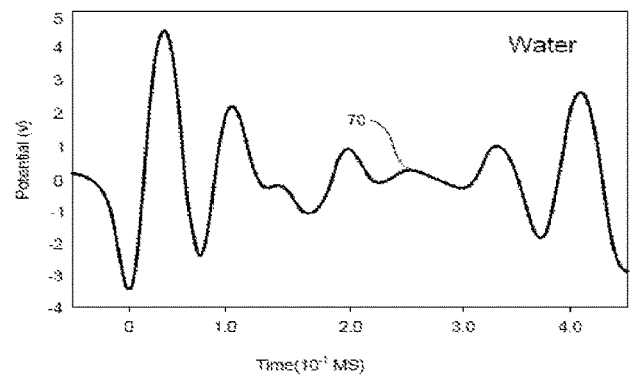
FIG. 2B illustrates known waveforms for water.
Figure 3:
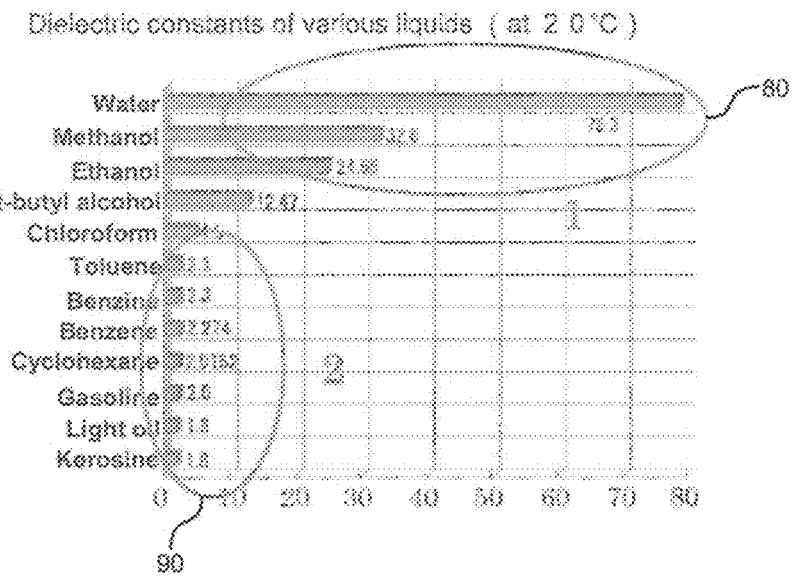
FIG. 3 illustrates a table of known dielectric constant values of various liquids.
Figure 4:
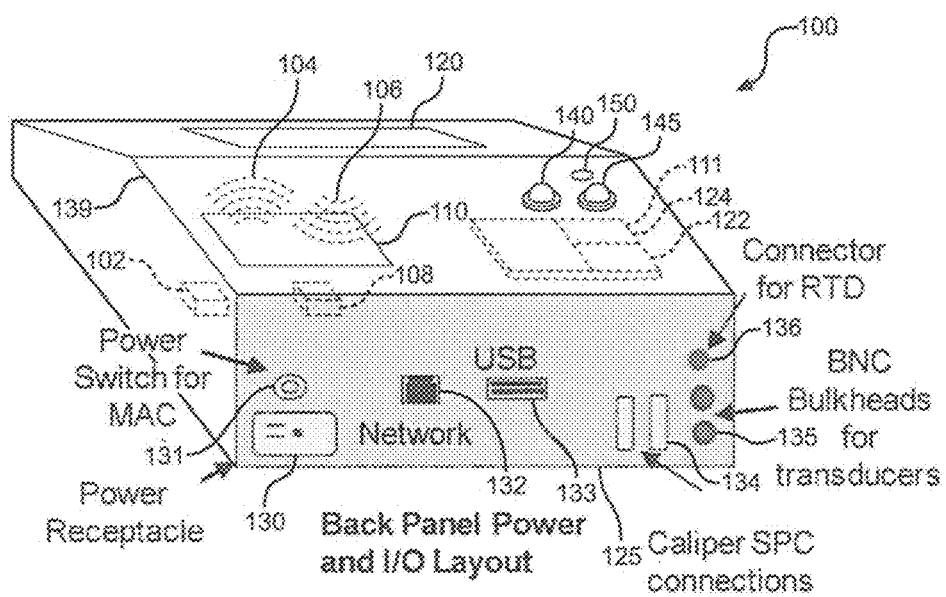
FIG. 4 illustrates relative positioning of primary components of an example screening device.
Figure 5:
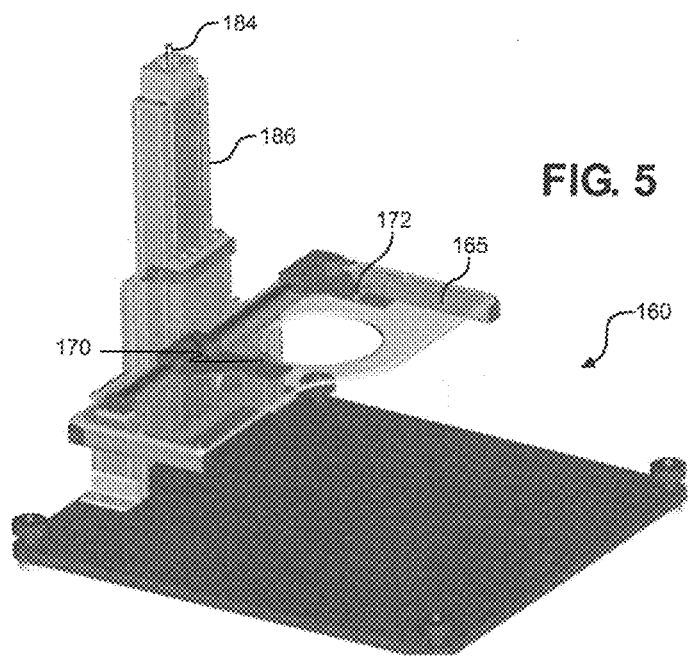
FIG. 5 illustrates an example base for an example screening device.
Figure 6:
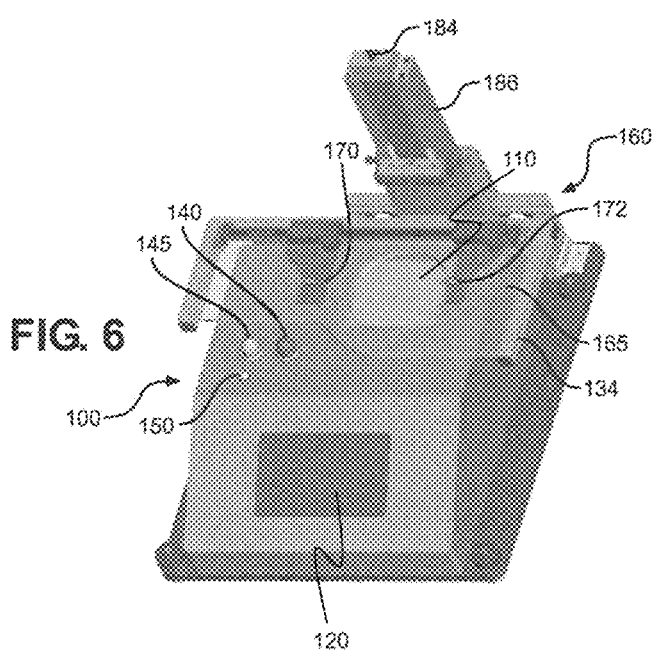
FIG. 6 illustrates a combined example screening system and example base.

FIGS. 4-8 illustrates a representation of an RF and ultrasonic screening system. Screening device 100 may be physically similar to sensing device 10 illustrated in FIG. 1. However, screening device 100 may uses different algorithms to analyze contents of container 30. Screening device 100 may also function by having a transmitting antenna 102 emit a radio frequency pulse or sending signal 104 which may be scattered by liquid in a glass or plastic container (not shown in FIG. 4). A scattered sending signal may reflect back from a liquid as a receiving signal 106 and may be picked up by signal receiving antenna 108. Signal receiving antenna 108 may send receiving signal 106 for processing by a processing unit 111 for performing a predetermined computation on averaged waveforms in receiving signal 106. Processing unit 111 may be a computer that controls portions of screening device 100 and may provide a user interface via the User Interface Touch Screen 120. Processing unit 111 may also include a database 122 and a comparison device 124 and may be sufficiently programmed and configured to execute scanning methods described in more detail below. Screening device 100 may include a back panel 125 that may have various connections and switches such as a power receptacle 130 adapted to receive electrical power, a power switch 131, an Ethernet connection 132, a USB connection 133, caliper statistical process control (SPC) connections 134, bayonet (BNC) bulkheads for transducers 135 and a connector 136 for resistance temperature detectors (RTD). A top surface 139 may support sensing pad 110 along with a hazard light 140, a safe light 145, and a power light 150.

FIGS. 5-8 illustrate a view of an example ultrasonic sensor positioning system 160. Positioning system 160 is illustrated alone in FIG. 5 and with screening device 100 in FIGS. 6-8. A clear z-plate 165 may control a vertical position of ultrasonic transmitter 170 and ultrasonic receiver 172 and temperature sensor 174 best illustrated in FIG. 8. Z-plate 165 may serve as holder for supporting a container with a liquid sample. Using a hand-crank 182 at a top portion 184 of vertical assembly 186 may move z-plate 165. Temperature sensor 174, ultrasonic transmitter 170, and ultrasonic receiver 172 may be moved in and out by an operator to ensure that temperature sensor 174 is located near container 190 being interrogated, while ultrasonic transmitter 170 and ultrasonic receiver 172 are in intimate contact with container 190. Digital micrometers 192 and 196 may track a horizontal separation of ultrasonic transmitter 170 and ultrasonic receiver 172 so that velocity may be calculated as a separation distance divided by a measured transmission time. Ultrasonic transmitter 170 and ultrasonic receiver 172 may also use a delay line to create a time difference or phase shift between ultrasonic signals transmitted from ultrasonic transmitter 170 and ultrasonic receiver 172. A short pulse may be transmitted to one side of container 190 and a response may be measured on an opposite side of container 190 when being inspected. In one embodiment, ultrasonic transmitter 170 and ultrasonic receiver 172 are a dedicated transmitter on one side of container 190 and dedicated receiver on another side of container 190. In another embodiment, ultrasonic transmitter 170 is an ultrasonic transducer on one side of container 190 that may either transmit or receive ultrasonic signals, and ultrasonic receiver 172 is an ultrasonic transducer on another side of container 190 that may either transmit or receive ultrasonic signals. In another embodiment, one of ultrasonic transmitter 170 or ultrasonic receiver 172 is used as a single ultrasonic transducer that is used alone to both transmit and receive ultrasonic signals. In another embodiment, ultrasonic transmitter 170 and ultrasonic receiver 172 are both on a same side of container 190.

General Operation

Figure 7:
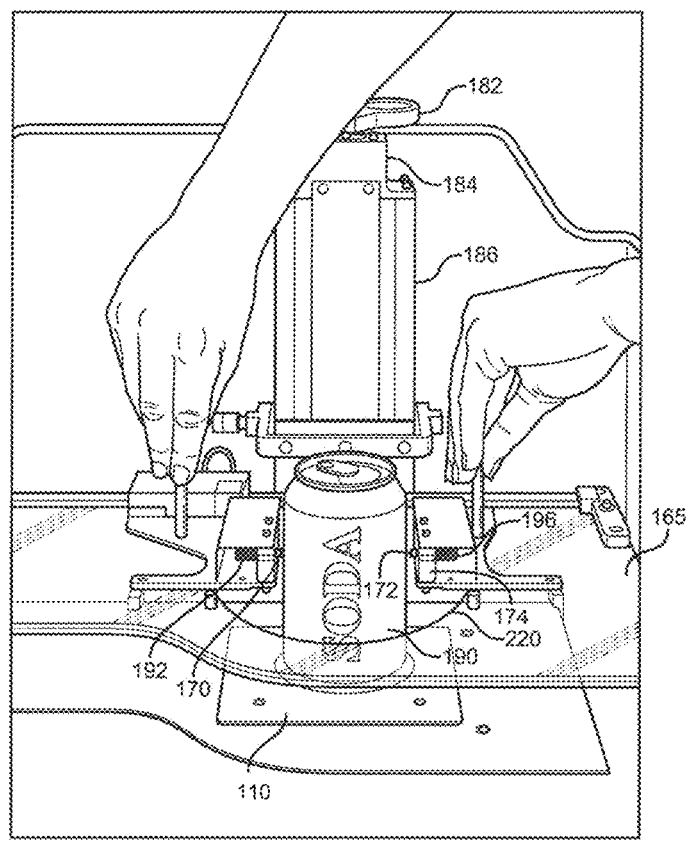
FIG. 7 illustrates a container positioned in an example base/screening system combination.
Figure 8:
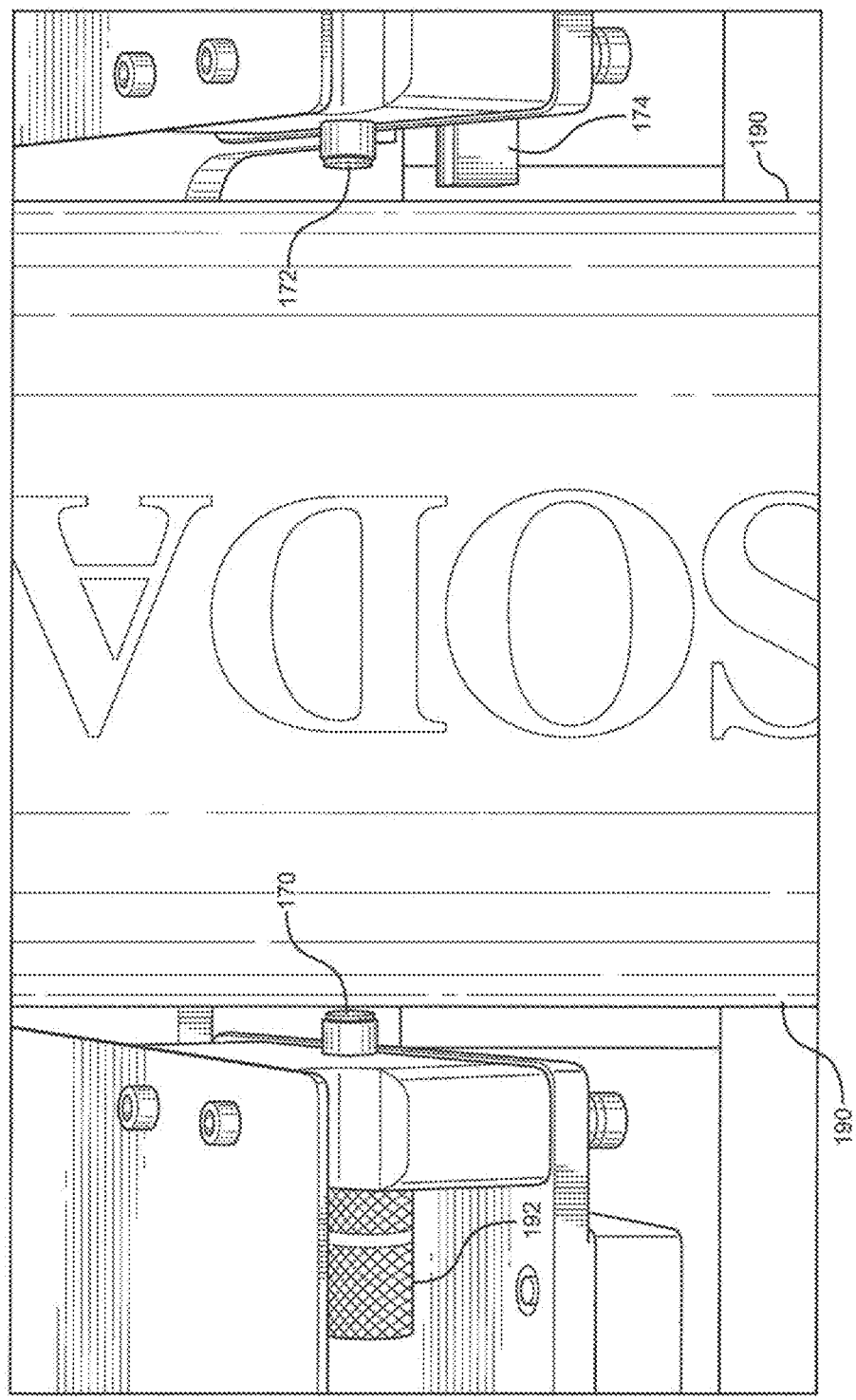
FIG. 8 illustrates an example ultrasonic screening system near but not in contact with a container.
Figure 9:
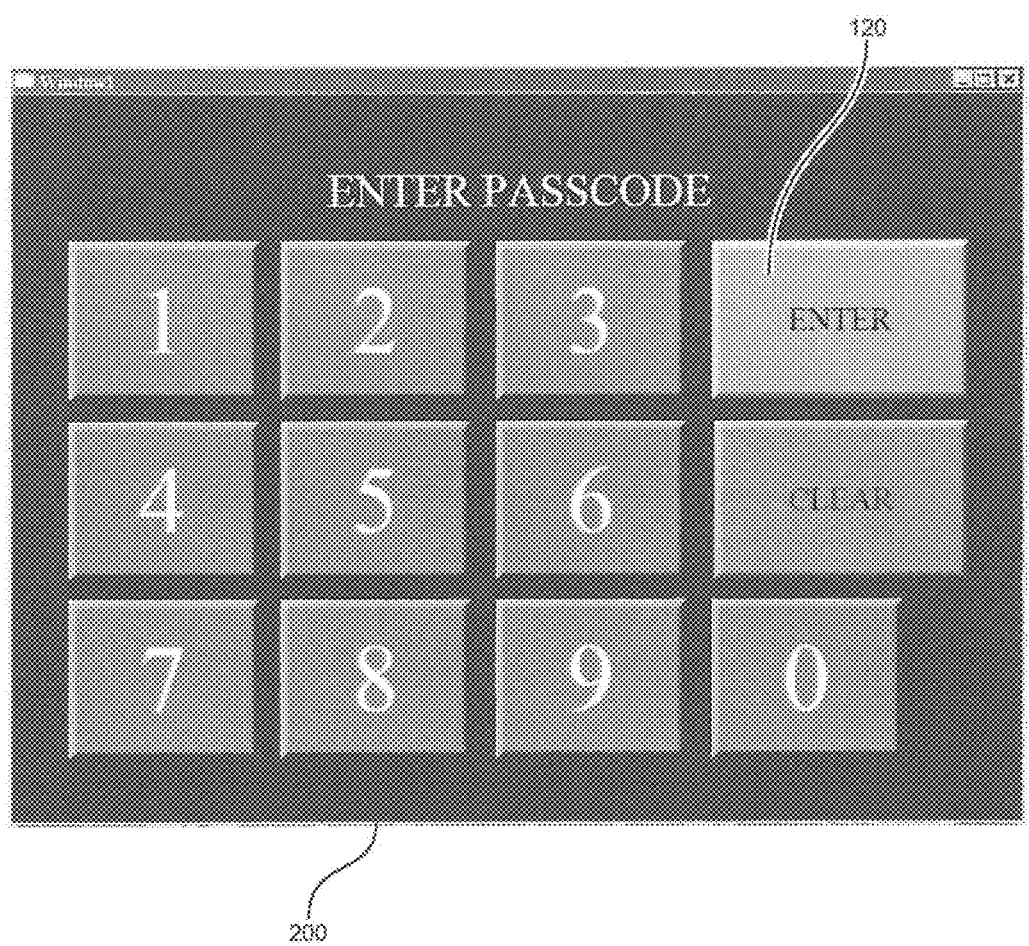
FIG. 9 illustrates an example user interface screen for an example screening system.
Figure 10:
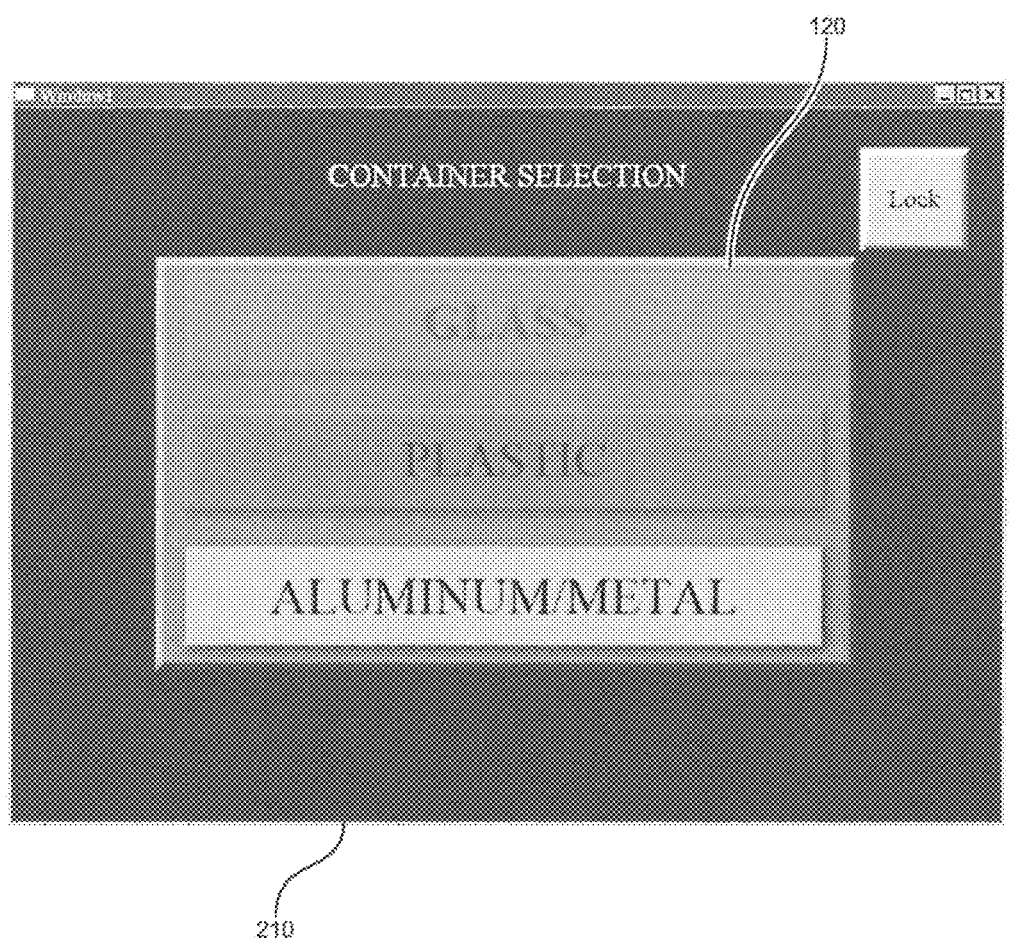
FIG. 10 illustrates an example screen shot of a user interface.
Figure 11A:
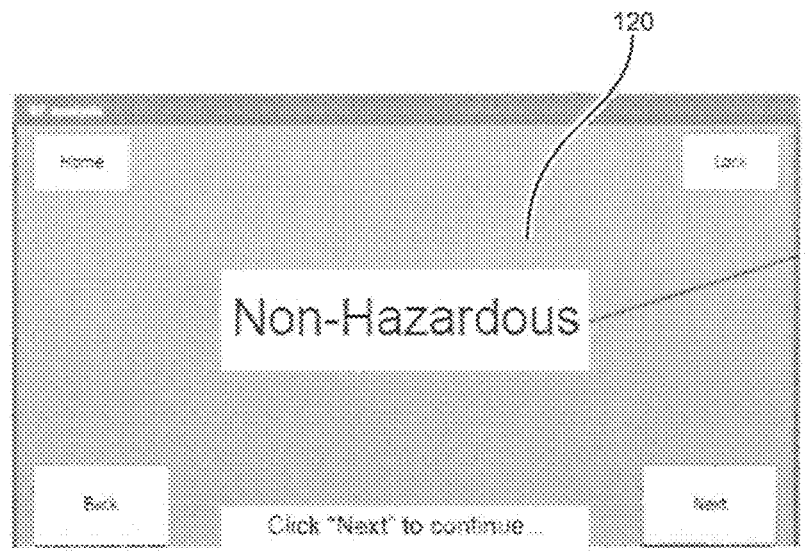
FIG. 11A illustrates an example screen shot for non-hazardous liquids.
Figure 11B:
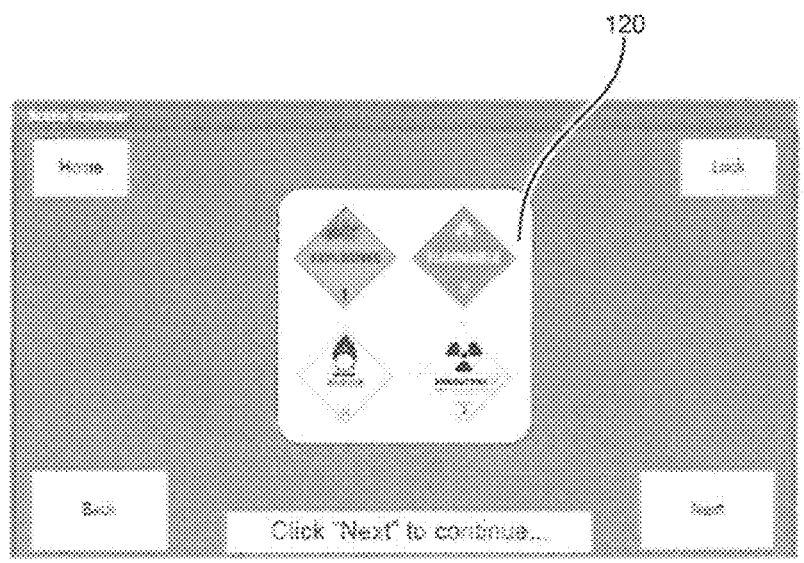
FIG. 11B illustrates an example screen shot for hazardous liquids.

An operator may be required to enter a passcode, via touch screen 120, to access a functionality of screening device 100. A screen shot of a passcode interface 200 is illustrated in FIG. 9. An operator may be required to enter a type of container using a selection interface 210 similar to example interface illustrated in FIG. 10. As best illustrated in FIG. 7, after selecting a type of container, an operator will place container 190 on sensor pad 110 by inserting container 190 through a large opening 220 in z-plate 165. An RF measurement may be made within two seconds of container 190 being placed on pad 110. An operator may then be required to adjust a height of z-plate 165 until a laser pointer (not shown) is on a smooth region of container 190. An operator may then move ultrasonic transmitter 170 and ultrasonic receiver 172 toward container 190 until contact is made. Screening device 100 may then alert an operator when sufficient contact has been made, and screening device 100 may illuminate either safe light (green) 145 or threat light (red) 140 to alert an operator. An operator may then move ultrasonic transmitter 170 and ultrasonic receiver 172 away from container 190 to ensure that ultrasonic transmitter 170 and ultrasonic receiver 172 are not touched and damaged as container 190 is removed from screening device 100. A threat/non-threat signal may also appear on user interface screen 120 in a means similar to the screenshot of FIGS. 11A and 11B.

Figure 12A:
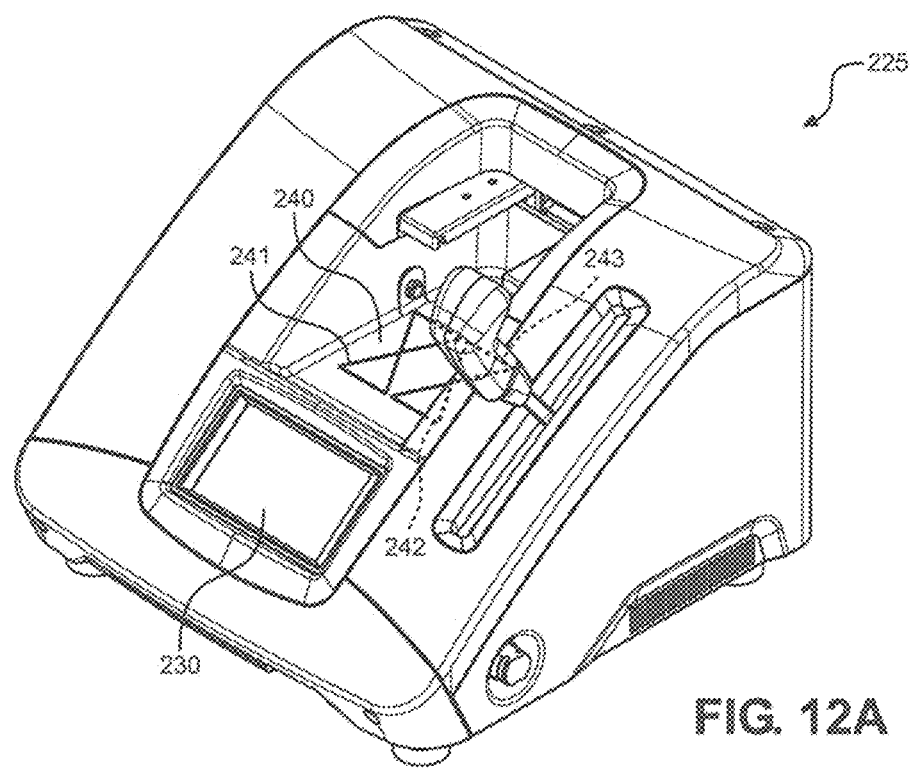
FIG. 12A illustrates an example screening system.
Figure 12B:
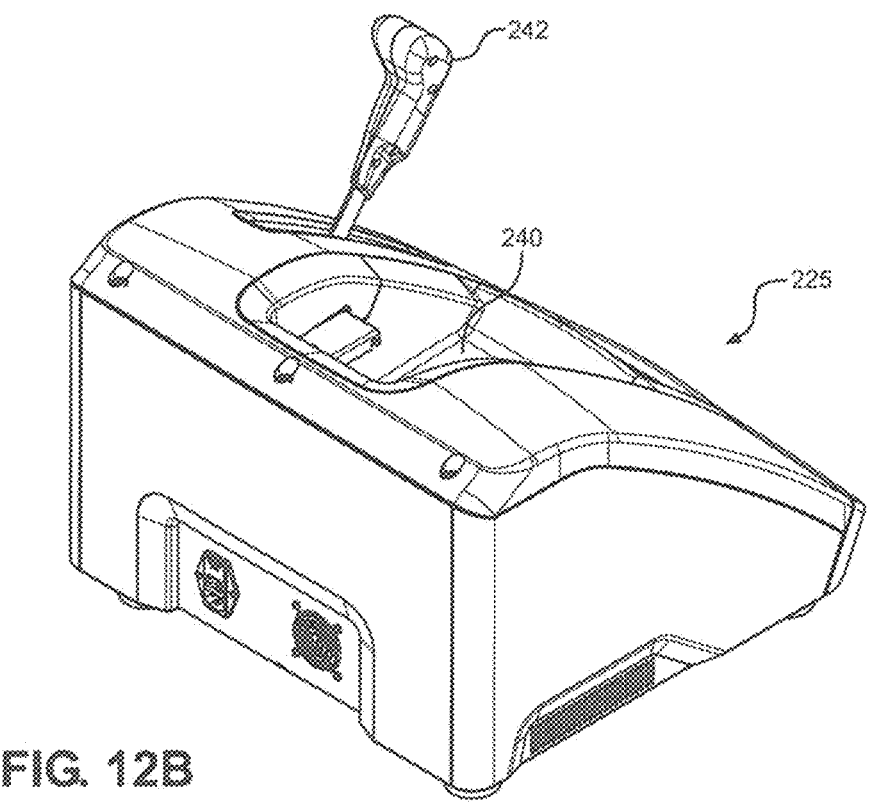
FIG. 12B illustrates an example screening system.

FIGS. 12A and 12B illustrate an alternative example embodiment of a screening system 225 with a touch screen 230, a sensing pad 240 and two bowtie RF antennas 241, 242. Screening system 225 may incorporate both ultrasonic and RF sensors into a single housing and works in a similar manner to screening device 100 and ultrasonic sensor positioning system 160 and thus will not be described separately. However, there may be some differences between screening system 225 and screening system 100. For example, when a container is placed on pad 240 of screening system 225, a lever 243 may be used to move ultrasonic sensors into contact with a container. Pad 240 may serve as a holder for supporting a container with a liquid sample. Screening system 225 may be configured to execute algorithms described below in more detail below regarding detecting placement of a container, determining a type of container, and detecting hazardous liquids within a container.

Combined Ultrasonic/RF Interrogation

A screening system may incorporate modifications by including hardware and software that may add flexibility and provide a wider application base for screening. Modifications may enable an automatic detection of a container placed on pad 110, 240 and an automatic determination of materials that form a container placed on pad 110, 240. In addition, a database of liquid signatures may be used to more accurately identify unknown liquids.

A. General Algorithms

Several different time domain based algorithms may be used to detect information about a liquid container. A pair of co-located bowtie antennas 241, 242 are illustrated in FIG. 12A. One antenna 241 may transmit impulsive RF energy and another antenna 242 may receive high-speed, short duration samples, and may produce a characteristic reflection signal 300 illustrated in FIG. 13. Characteristic reflection signal 300 may change depending upon liquid contents of a container placed on RF pad 240. A baseline signal, known as an "empty tray" signal, may be a basis of comparison and may be constantly updated when no container is present on pad 240. All algorithms described below may be normalized to an "empty tray" signal which may serve to eliminate a majority of unit-to-unit variations. In each algorithm, reflection signal 300 developed from transmit/receive pair of bowtie antennas 241, 242 may be analyzed. By comparing various characteristics of reflection signal 300 from a container with liquid to another reflection signal 300 from a container with no liquid, or absence of container, also known as the "empty tray" signal, using combinations of several different algorithms, numerical results determine a presence of a container, a container material, and an identity of a container's contents.

Figure 13:
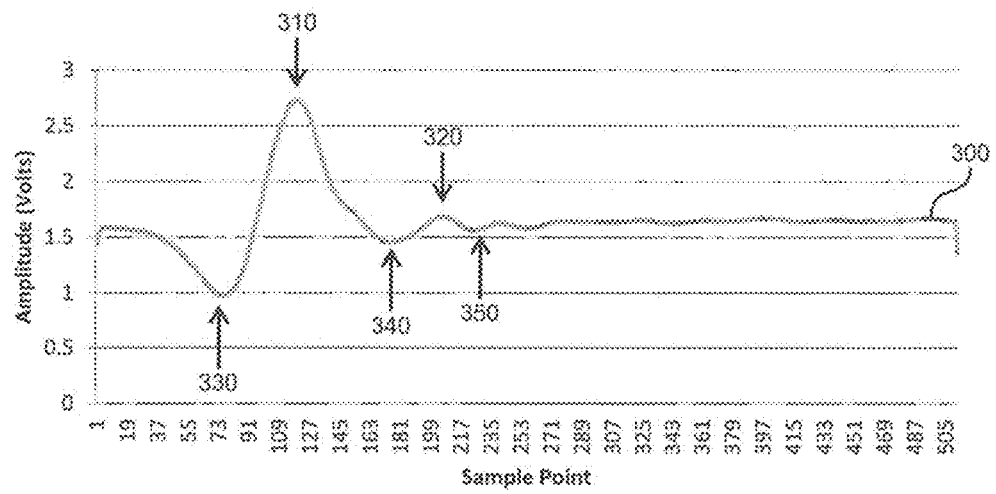
FIG. 13 illustrates an exemplary RF signal trace.

In general, all algorithms may require an amplitude and sample number of first two maxima 310, 320 and first three minima points 330, 340, 350 illustrated in FIG. 13. First minimum point 330 may serve as an absolute starting data point upon which all algorithms are referenced. Data to a left of first minimum point 330 may not be used. From first minimum point 330, only 400 points of data to a right of first minimum point 330 may be used.

Algorithm #1: Normalized Peak Location Shifts

Upon placement of a liquid container on RF pad 240, both an amplitude and a position of first 330, and second 340 minima points, and first 310, and second 320 maxima points may change with respect to an empty tray signal. Shifts in a location of first 310, and second 320 maxima points with respect to the empty tray signal are normalized.

Where a difference in liquid sample location of the second peak 320 and a liquid sample location of the first peak 310 may be divided by a difference of peak locations of an empty tray signal. This results in a fractional change in peaks with respect to an empty tray signal.

Algorithm #2: Normalized Triangular Attributes

Figure 14:
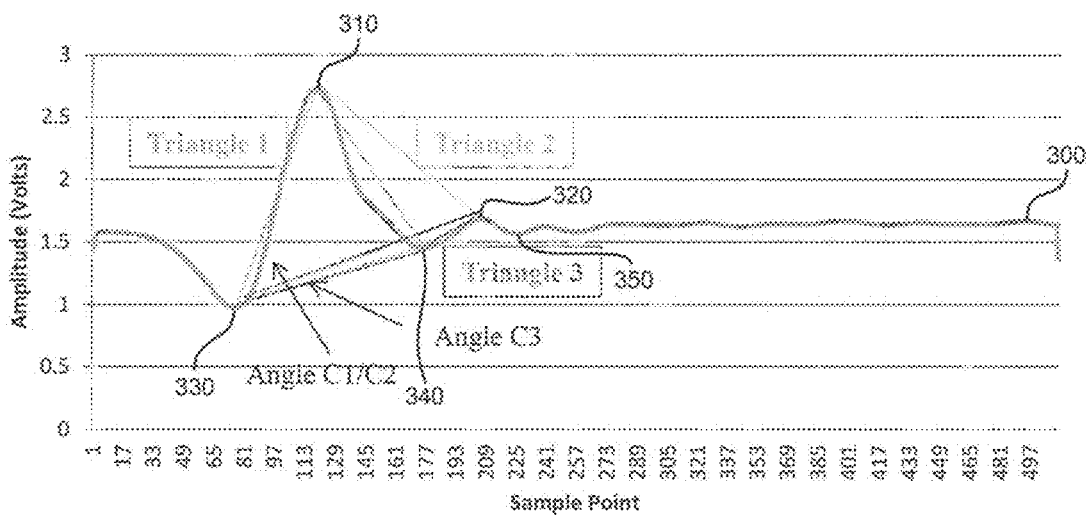
FIG. 14 illustrates an exemplary RF signal trace and triangles used for trace analysis.

This algorithm may be based upon three general triangles constructed between minimums 330, 340, and 350 and peaks 310 and 320 as illustrated in FIG. 14. Triangle 1 may use first minimum 330 and first maximum 310 plus second minimum 320 to form three sides of Triangle 1. Triangle 2 may use first minimum 330 and first maximum 310 plus second maximum 320 to form its three sides. Triangle 3 uses first minimum 330 and second maximum 320 plus second minimum 340 to form its three sides. Using general triangle theory, an angle formed at first minimum point 330 for all three triangles is calculated and normalized to corresponding empty tray signal angles. In addition, an area enclosed by each triangle may be calculated and normalized to an empty tray signal. A ratio of normalized triangles may be calculated.

Algorithm #3: Normalized Slope

This algorithm may require an amplitude and position (data point) of first minimum 330 and second minimum 340. Liquid samples placed upon RF pad 240 may not only affect an amplitude of first two minima 330, 340 but also locations of minima 330, 340. Slopes for each sample may be normalized to a corresponding empty tray signal slope.

Algorithm #4: Normalized Power in Two Regions

Figure 15:
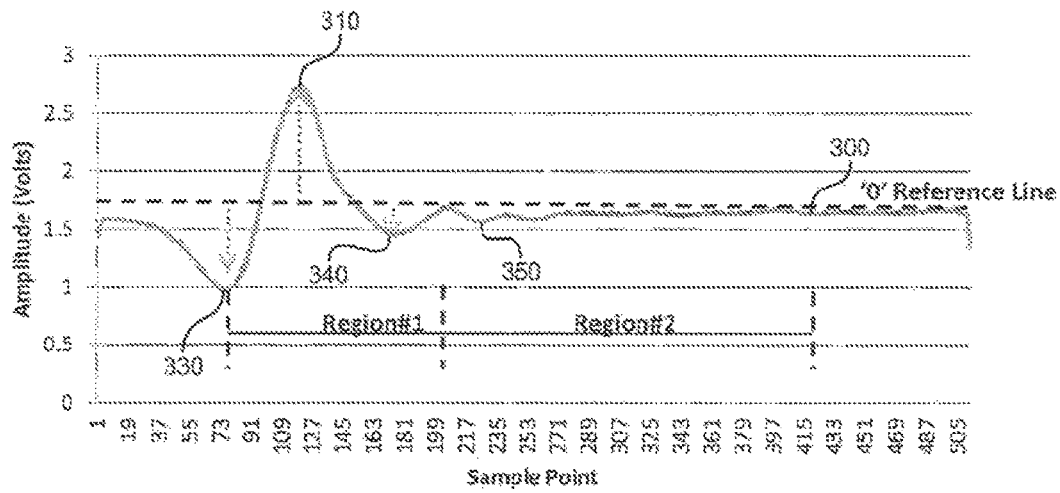
FIG. 15 illustrates an exemplary RF signal trace divided into regions.

This algorithm may use a square of differences for each sample of a reflected signal from a '0' reference point set at 1.67 volts as illustrated in FIG. 15. There may be two distinct regions determined by 150 data points from first minimum 330 for Region#1 and 100 data points from an end of Region#1 which forms Region#2. Since squaring an amplitude of a time domain signal is proportional to power, algorithm #4 measures a relative power contained in reflection signal 300. As before, power in each sample is normalized to an empty tray signal power.

Algorithm #5: Summation of Region#2 Standard Deviations Differences

This algorithm may use the last 225 to 300 data points in reflected signal 300, as illustrated by Region#2 in FIG. 15, and may calculate a mean and standard deviation for each sample and determine a difference between samples and an empty tray signal. A mean of an empty tray signal may be calculated first and then a difference between each sample data point and an empty tray signal mean may be calculated. Two terms are used, a standard deviation difference between a sample and empty tray signal, and a sum of differences for each data point and empty tray signal mean.

Algorithm #6: Cross Correlation Function

This algorithm may use Region#1 and Region#2 illustrated in FIG. 15 and may calculate a magnitude of a cross correlation of a liquid sample with an empty tray reflected signal. The following formula (1) shown below may be used:

$$\mathrm{Correl}(X,Y) = \Sigma(X-X_m)*(Y-Y_m)/\sqrt{\Sigma(X-X_m)^2 * \Sigma(Y-Y_m)^2} \quad (1)$$

Where $X_m$ and $Y_m$ may be means of a sample and empty tray signal and X and Y are data points.

Algorithm #7: Normalized First and Second Peaks

This algorithm may take a ratio of a liquid sample's first peak to an empty tray signal's first peak, and likewise a liquid sample's second peak to an empty tray signal's second peak.

B. Detecting Placement of Container Using RF Signatures

Figure 16:
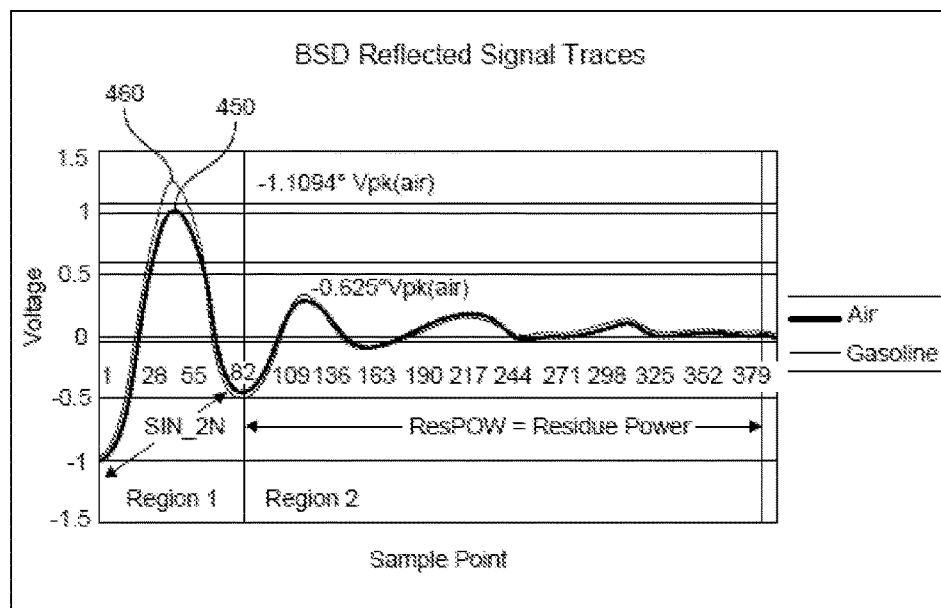
FIG. 16 illustrates exemplary RF signal traces.

With reference again to FIG. 4, when sensing device 100 is turned on, a baseline empty tray reflected waveform may be generated by having a transmitting antenna 102 emit a radio frequency pulse or sending signal 104 when no container is present on pad 110. Air present around screening device 100 may scatter sending signal 104 and may produce receiving signal 106 which is used as an empty tray baseline for comparison with other signals. Empty tray baseline may be continuously or intermittently determined. Alternatively, determining a baseline may be based on reflected signal 450, as illustrated in FIG. 16, which may be generated by testing a container filled with only air. Baseline reflected signal waveform 450 may then be stored in database 122 and may be constantly updated. When container 190 is tested with an unknown liquid, a reflected signal such as waveform 460 may be generated. Waveforms 450, 460 may be plotted as a trace as illustrated in FIG. 16 which may also show a calculated normalized slope SIN_2N.

Figure 17:
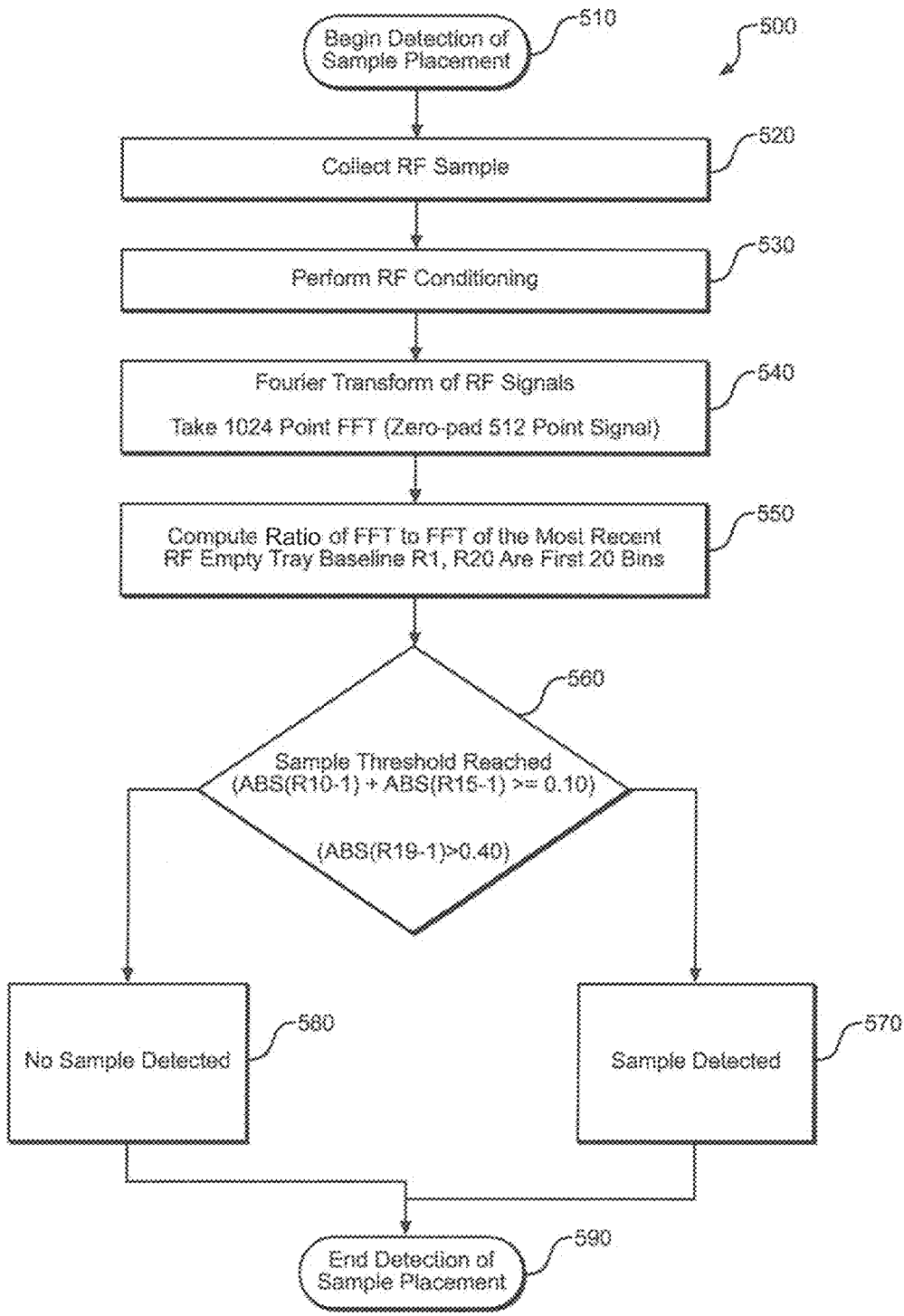
FIG. 17 is a flowchart showing steps of an example algorithm for detecting sample placement.

A flowchart showing various steps of a sample detecting algorithm 500 is illustrated in FIG. 17. Sample placement detection algorithm 500 begins at step 510. Next, RF receiving signal 106 may be collected at step 520 when no container is present on sensing pad 110 to determine an RF empty tray baseline. Next, the RF receiving signal 106 may be monitored further and sent to processor 111 where signal 106 may be conditioned at step 530. Processor 111 may then conduct a discrete Fourier analysis to convert a baseline into the frequency domain as a baseline transform at step 540. Specifically, a 1024 point fast Fourier transform may be conducted. Values of a baseline transform at selected frequencies or frequency bins may be stored in memory 122. When sensing device 110 is in use, processor 111 may continuously activate transmitting antenna 102 to transmit sending signal 104 and monitor receiving signal 106. Receiving signal 106 may be continuously subjected to a Fourier analysis and continuous transform values may be generated at the same selected frequencies or frequency bins used for baseline transforms. A ratio of continuous transform values to baseline transform values may be computed at step 550. For convenience, ratios calculated for a first 20 bins may be labeled R1-R20. When a ratio exceeds a predetermined threshold at step 560, sensing device 100 may determine with a high degree of confidence that a container may be present on pad 110 at step 570 or not detected at step 580. Algorithm 500 continuously repeats until stopped by a user at step 590. Algorithm 500 may be used to determine if a container is present but may also be used to determine if a container is full of liquid or empty.

C. Container Material Identification

Figure 18A:
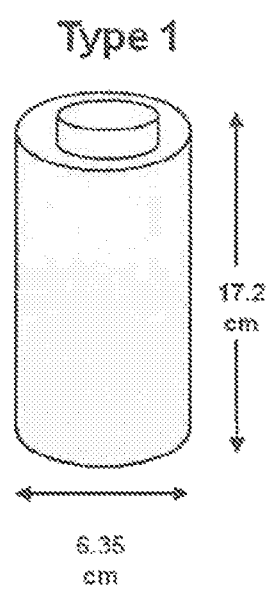
FIG. 18A illustrates an example container utilized in connection with RF testing analysis.
Figure 18B:
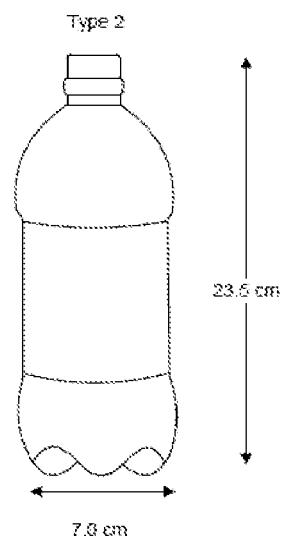
FIG. 18B illustrates an example container utilized in connection with RF testing analysis.
Figure 18C:
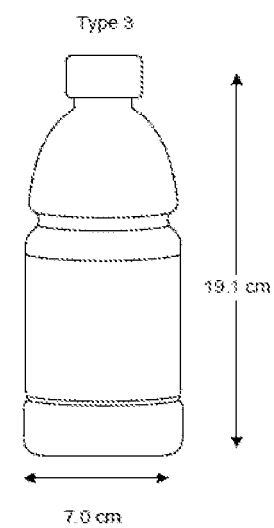
FIG. 18C illustrates an example container utilized in connection with RF testing analysis.

Inputs from both RF signal receiving antenna 108 and ultrasonic sensor 172 may be used to detect whether a container is made of plastic, metal or cardboard. Different types of containers are illustrated in FIGS. 18A, 18B and 18C. In order for screening device 100 to make an accurate determination of an unknown liquid, a material used for a container holding the unknown liquid must be known. Since an operator might misidentify a material forming a container, an identifying method may be programmed into screening device 100 to automatically identify a material from which a container is formed and overrule an operator's input when necessary. Initially, a determination may be made as to whether or not container 190 is metal. When a container made of unknown material is sensed as being present on pad 110, transmitting antenna 102 may send a radio frequency pulse or sending signal 104. Reflected signal 106 may then be analyzed. Specifically, reflected signal 106 may be analyzed to determine if First Peak Saturation and First Min Change is less than 0.40 V, which may indicate a presence of metal.

Additionally, receiving signal 106 for an unknown material may be subjected to a Fourier analysis, and transform values may be generated at the same selected frequencies or frequency bins used for a baseline transform described above with regard to detecting placement of container using RF signatures. Ratios of transforms may be calculated at selected frequencies or frequency bins and then input into a Partial Least Squares Algorithm. Measurements of signal 106 in a time domain as described above in Algorithms 1-7 may also be input into a Partial Least Squares Algorithm. Results generated by a Partial Least Squares Algorithm may be used to determine if container 190 is made of metal. Outputs from a Partial Least Squares Algorithm at certain frequency bins are checked to determine if outputs exceed a preset threshold, thus indicating a presence of metal. For example, a Partial Least Squares value less than −0.05 and an output ratio R8 from the $8^{th}$ bin lower than a threshold value of 0.75 indicates a presence of metal.

A presence of glass versus plastic may be determined in various ways by analyzing an output from ultrasonic sensor 172. The ultrasonic signal may be checked using various techniques. An inversion of an ultrasonic signal at a delay line caused by a container interface may be used to detect a glass container. A reflection found in an ultrasonic signal associated with a container thickness is an indication of glass. Similarly, a shift in an ultrasonic signal's reflected peak may be tracked since, with a glass container, a dry couplant at an end of a delay line compresses when brought into contact with a ridged glass container. A behavior of a reflected Hilbert transform of a delay line peak may be associated with a particular container material. A decrease in amplitude with a leftward shift or an increase with no shift may indicate plastic. An increase in amplitude with a shift may indicate glass.

Another technique may involve measuring a diameter/thickness of container 190 when an ultrasonic measurement is made. Digital micrometers 192, 194 may measure a diameter, when an ultrasonic test begins, and again when delay lines first come into contact with container 190 but before an ultrasonic measurement is completed. A difference in two diameter measurements may be used to determine how ridged container 190 is, and thus determine if a container is glass or plastic.

When detecting cardboard, a combination of RF and ultrasonic signals may be used. RF signals may be used to detect metal foil linings in cardboard boxes while a change in diameter may also be checked to determine if a container is soft. A soft container with a foil liner may be determinative of a cardboard container.

D. Using RF, Ultrasonic and/or Temperature to Identify Liquids of Interest

Ultrasonic Interrogation

In one embodiment, an ultrasonic system operates at a 10 MHz frequency and transmitter 170 continually transmits a single pulse of ultrasonic (mechanical) wave energy. Most of the energy may be coupled into container 190 and a portion of the energy creates a wavefront that emanates from transmitter 170. Receiver 172 on an opposite side of container 190 may receive a transmitted pulse, which is now distorted, but not so much as to cause problems. Electronics in screening device 100, such as those in computer 111, may measure a time between a transmitted pulse and a received pulse. This time-of-flight result may be combined with a measurement of a sensor separation value to determine a wave velocity. In screening device 100, digital micrometers 192, 194 may measure a distance between transmitter 170 and receiver 172. A wave velocity may then be calculated as a measured distance divided by a time between a transmission of a pulse and its reception. This wave velocity may be used as a discriminant. Many liquid velocities may be very similar to that of water. Threat liquids, such as alcohol and gasoline, may be very different. A reflection mode may also be applied from a transmitter side of container 190 to assist in determining a nature of container 190. Further, a pulse-echo mode may be established to determine container thickness. In connection therewith, a delay line may be employed to increase a near surface resolution of a thickness measurement, thereby providing a more accurate evaluation of a container wall thickness and ultimately leading to a more accurate velocity determination.

There is an established relationship between acoustic velocity values and a chemical constitution of a liquid. A number of relationships that express a dependence of ultrasonic wave velocity on chemical composition and molecular structure were developed from these observations. One relationship that may expresses a dependence of an ultrasonic wave velocity, C, on quantities governing a chemical constitution of liquids (derived from van der Waal's equation of state) may be given by the formula (2):

$$C = \left[\frac{\gamma RT}{M - b*\rho}\left(\frac{M}{3(M - b*\rho)} - 2\right)\right]^{\frac{1}{2}} \quad (2)$$

where R is a gas constant, T is an absolute temperature, M is a molecular weight, b is a van der Waal's co-volume constant, γ is a ratio of specific heats, and ρ is a mass density. Both a theoretical dependence of velocity on a molecular structure, arising from chemical constituents, and phenomenological observations may provide a sound technical foundation for expecting a consistent correlation between a measured velocity and chemical composition. A use of wave velocity to discriminate between hazardous and innocuous liquids (in sealed and unsealed containers) may have a theoretical and an empirical basis. A wave velocity may also be a function of temperature in both liquids and solids. Therefore, bottle screening device 100 measures a temperature of a liquid sample. Temperature dependencies of liquids are known, so temperature change may be compensated for. Temperature dependence of velocity may be linear to a first order approximation. Typical velocity temperature coefficients for metals, polymers, glass, and liquids are provided in Table 1 below.

TABLE 1

Velocity/Temperature Coefficients for Selected Solids and Liquids

| Material | Velocity Temperature Coefficient $\Delta V/\Delta T$ (m/sec/° C.) |
|---|---|
| Metals | +0.2 to +06 |
| Polymers | +9.0 to +15.0 |
| Glass (SiO$_2$) | +0.6 |
| Organic Liquids | −2.7 to −4.8 |
| Aqueous Liquids | 0 to +3.6 |

More specifically, a velocity of an ultrasonic wave in a metal or plastic may be a function of temperature. A temperature of metal or plastic near an interface between a metal or plastic vessel wall and gas or liquid contents, may be a function of heat transfer across an interface from a hot vessel wall to a cool gas or liquid. A rate of heat transfer due to conduction may be a function of thermal conductivity of gas or liquid contents. A thermal conductivity of contents depends on a composition of the contents (e.g., K(air) =0.0140, K(ethane)=0.0106, K(methane)=0.0175, K(water) =0.343. Thus, measuring a time rate of change in a critical angle of reflection or a velocity of an ultrasonic wave near a vessel wall/contents interface may provide a non-invasive means of determining whether contents are liquid, air, or a gas. It may also be possible to determine a type of liquid (e.g., oil or water). If a vessel wall is a metal, inductive heating of a metal vessel wall to generate a temperature gradient at a vessel wall/contents interface may be accomplished using a high-current, low frequency eddy current coil. If a vessel wall is plastic, microwaves may be used to heat a plastic vessel wall. Piezoelectric sensors may be used to measure a time rate of change in velocity in metal or plastic due to heat transfer from a container to contents, or to measure a change in critical angle of a reflected ultrasonic wave from an interface.

Temperature coefficients may represent fractional velocity changes per degree centigrade of approximately 0.01 percent for metals and glasses, 0.5 percent for polymers, and 0.25 percent for liquids. A velocity temperature coefficient may be positive for solids and aqueous solutions, while non-aqueous solutions may have a negative temperature coefficient. Because an aluminum can wall thickness may be thin (i.e., a small fraction of a container diameter), temperature coefficients of container materials may not have a significant effect on a time-of-flight measurement. However, temperature coefficients for liquids may be taken into account because of large velocity errors that may occur if temperature coefficients were not accounted for.

Many velocity measurement methods involving resonance and spectral modulation may have a number of experimental constraints related to the geometry of a propagation medium. One approach that is robust and simple, may be to measure two independent parameters: transit time, or time-of-flight of an elastic wave pulse; and a corresponding path length of the pulse. Both pulse-echo and through-transmission modes may be used to measure time-of-flight. During previous investigations, pulse-echo mode was used to measure time-of-flight in a container wall, and through-transmission mode was used to measure time-of-flight through a container and its contents. Using pulse-echo mode time-of-flight measurement may enable an effect of a container wall thickness and material to be removed from through transmission time-of-flight data. This isolation of a container's effect allows a time-of-flight of an ultrasonic wave in contents of a sealed container to be determined independently of container wall composition and thickness.

An ultrasonic velocity in an unknown liquid may be calculated using formula (3):

$$C = \frac{D - c_{wall}(T_{wall1} + T_{wall2})}{T_{Total} - (T_{wall1} + T_{wall2})} \quad (3)$$

where D may be an outside diameter of a container, $c_{wall}$ may be an assumed propagation velocity in a container wall, $T_{wall1}$ may be a one-way propagation time for one container wall (measured by pulse-echo), $T_{wall2}$ may be a propagation time for another container wall, and $T_{Total}$ may be a total propagation time across a container (measured via through-transmission techniques).

RF Interrogation

An RF system may also be used to develop a signature of various hazardous liquids. Specifically, different liquids of interest may be analyzed to develop a signature for each liquid. Each liquid may be measured in containers made of different materials and sizes at different fill levels. RF signals reflected off of each liquid may be measured. Measurements may be taken in a time domain, and frequency domain, and may be used as inputs for a Partial Least Squares (PLS) algorithm to create PLS values associated with each liquid measured. PLS values, RF time and frequency measurements, ultrasonic wave velocities, and velocity temperature coefficients may act as a signature that uniquely identifies each type of liquid. A database 122 of liquid signatures may then be developed and used to identify unknown liquids or at least classify unknown liquids into certain categories. In each case, RF ultrasonic measurements may be temperature dependent so temperature signals from infrared sensor 174 may be used to compensate for changes to measurements due to temperature changes.

Measurements taken in a time domain may identify characteristics of an RF waveform from sensor 108. Measurements may be made of amplitude and index shifts. Comparisons may be made between measurements of an unknown liquid to baseline measurements, and also determine how different parts of a waveform change in relation to each other.

Measurements taken in a frequency domain may include 20 difference measurements and 20 ratio measurements. Difference measurements may be determined by calculating a difference between a first 20 frequency bins of a fast Fourier transform (FFT) taken of a baseline measurement taken with no container present, and a first 20 frequency bins of a fast Fourier transform taken of measurements of an unknown liquid. A calculated FFT may use a 512 point RF waveform padded with zeroes to allow a 1024 point transform to be calculated. Similarly, ratios may be determined by calculating a ratio of a first 20 frequency bins of a fast Fourier transform taken of a baseline measurement taken with no container present, and a first 20 frequency bins of a fast Fourier transform taken of measurements taken with an unknown liquid.

Once database 122 of signatures is developed, detecting if liquid in container 190 is hazardous may be conducted by measuring a sample unknown liquid to determine various parameters associated with the unknown liquid. Parameters may then be used to scan database 122 to determine if a sample unknown liquid matches any signatures stored in database 122. If parameters do not match any signatures, a clear result may be given. If parameters do match, a signature in a database device 100 may alert an operator and may display a name or category of a previously unknown liquid on screen 120. Inputs to PLS values may be dependent on a liquid to be identified. As new liquids to be identified are added to database 122, new PLS inputs may be created and current ones may be deleted.

Figure 19:
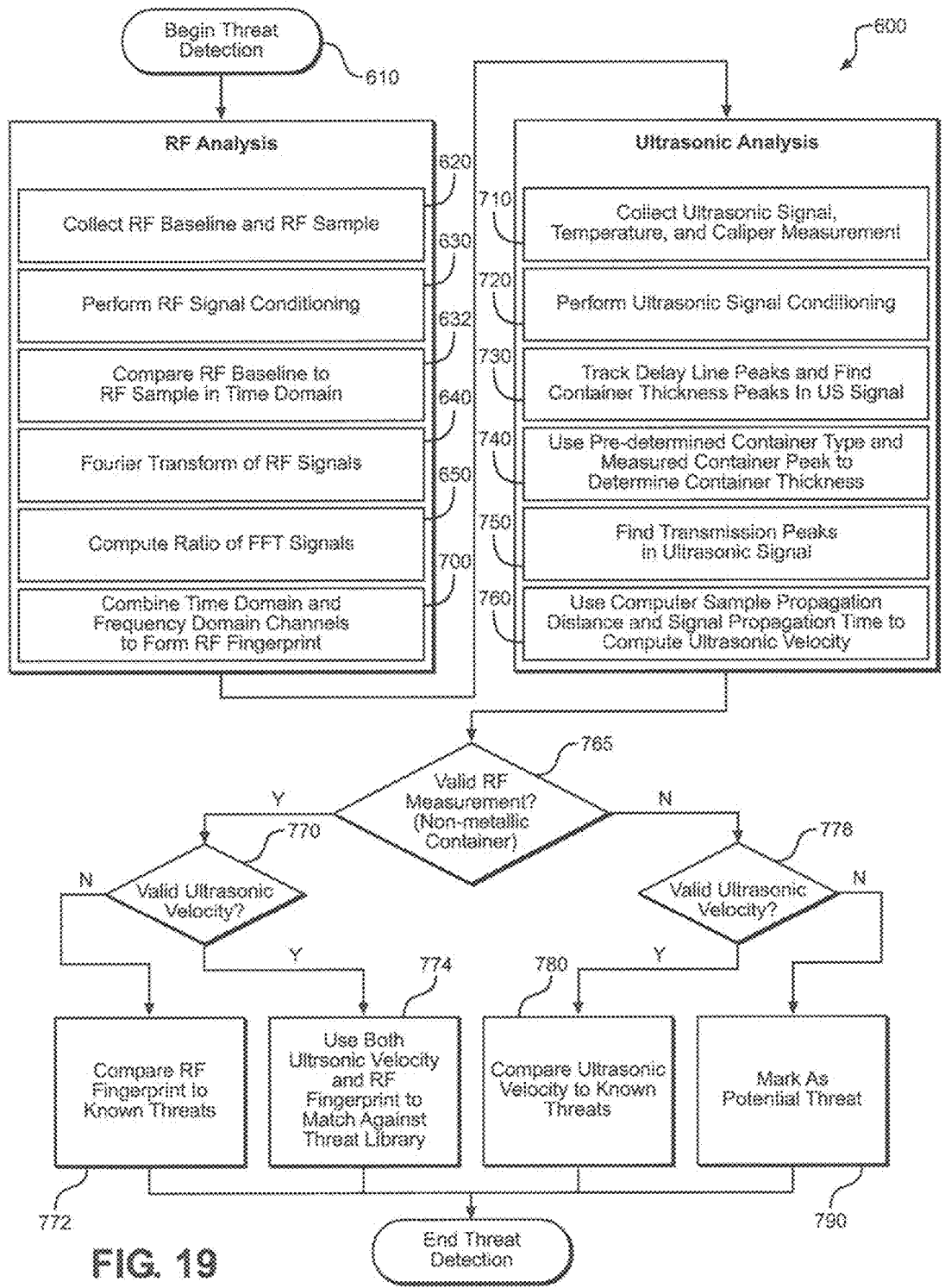
FIG. 19 is a flowchart showing steps of an example algorithm for detecting hazardous liquids.

A flow chart of a threat detection algorithm 600 is illustrated in FIG. 19 and may begin at step 610 with an RF analysis. In a manner similar to detection of sample placement algorithm 500, threat detection algorithm 600 may collect RF receiving signal 106 at step 620 when no container is present on sensing pad 110 to determine an RF empty tray baseline. Next, an RF receiving signal 106 may be monitored further and may be sent to processor 111 where signal 106 may be conditioned at step 630. An RF baseline signal and RF sample signals may be compared in a time domain at step 632. Processor 111 may then conduct a discrete Fourier analysis to convert a baseline signal and sample signal into a frequency domain as a baseline transform and a sample transform at step 640. Specifically, a 1024 point fast Fourier transform (FFT) may be conducted. Values of a baseline transform at selected frequencies or frequency bins may be stored in memory 122. Next, ratios of FFT transforms may be computed at step 650 and a signature may be formed at step 700.

Threat detection algorithm 600 may then perform an ultrasonic analysis starting at step 710 where an ultrasonic signal, temperature, and container size may be measured. Next, ultrasonic signal conditioning may be performed at step 720. An ultrasonic signal may then be analyzed to track delay line peaks and find container thickness peaks in an ultrasonic signal at step 730. A predetermined container type may be used at step 740 with measured container peak to determine container thickness. Next, at step 750 transmission peaks in an ultrasonic signal may be found, and ultrasonic velocity may be computed at step 760.

Since metal containers may not be measured with RF energy, algorithm 600 may check to see if a container is metallic to determine if an RF measurement is valid at step 765. With a valid RF measurement, a validity of an ultrasonic measurement may be checked at step 770. With an invalid ultrasonic measurement, algorithm 600 relies on an RF signature which may be compared to a database at 772 to determine known threats. With a valid ultrasonic measurement, both RF and ultrasonic measurements may be used to create a signature that may be compared to a database at 774, and algorithm 600 ends at step 775. Turning back to step 765, if no valid RF measurement is made, algorithm 600 may check for a valid ultrasonic measurement at step 778. With a valid ultrasonic measurement, an ultrasonic velocity may be used to detect a harmful liquid at step 780. With an invalid ultrasonic measurement at step 778, algorithm 600 may mark a liquid as a potential threat since neither RF measurements nor ultrasonic measurements are valid, and then algorithm 600 ends at step 775.

Testing

A. Non-Metal Containers

Table 7 and Table 8 provide identification numbers for 57 liquids in non-metal containers.

TABLE 7

Identification number and liquid identifier characterized in HDPE containers
HDPE Containers

| Number | Liquid |
|---|---|
| 1 | Tap Water |
| 2 | Coke |
| 3 | Saline Solution |
| 4 | Baby Formula |
| 5 | Fruit Punch |
| 6 | Distilled Water |
| 7 | Mouth Wash |
| 8 | Gatorade |
| 9 | Antifreeze |
| 10 | Liquid Fertilizer |
| 11 | IPA 91% |
| 12 | Ammonia |
| 13 | $H_2O_2$ 3% |
| 14 | Bleach |
| 15 | Gasoline |
| 16 | Diesel |
| 17 | Kerosene |
| 18 | E-85 |
| 19 | Paint Thinner |
| 20 | DeIcer |
| 21 | Acetone |
| 22 | Baby Oil |
| 23 | Gin 21% |
| 24 | Rum 21% |
| 25 | Sauvignon Blanc 13.4% |
| 26 | Bubble Bath |
| 27 | Chardonnay 14.1% |
| 28 | Vodka 21% |
| 29 | Merlot 13.5% |
| 30 | Mineral Oil |
| 31 | Tequila 21% |
| 32 | Southern Comfort 21% |
| 33 | Methyl ethyl ketone (MEK) |
| 34 | Mineral Spirits |
| 35 | Cabernet Sauvignon 13.5% |
| 36 | Tempranillo 12% |
| 37 | Vegetable Oil |
| 38 | Dry Rose 12.4% |

TABLE 8

Identification number and liquid identifier characterized in three container types

| Number | Liquid | Container |
|---|---|---|
| 39 | Vodka 40% | PP |
| 40 | SPF 50 Sunscreen | PP |
| 41 | Southern Comfort 40% | PP |
| 42 | SPF 60 Sunblock | PP |
| 43 | IPA 70% | PP |
| 44 | Dr. Pepper | PP |
| 45 | Cabernet Sauvignon | PP |
| 46 | Whiskey 40% | PP |
| 47 | Triple Sec | PP |
| 48 | Gin 40% | PP |
| 49 | Denatured Alcohol | PP |
| 50 | Nyquill (Cherry Flavor) | PETE |
| 51 | Nyquill (Original Flavor) | PETE |
| 52 | 50% $H_2O_2$ | HDPE |
| 53 | Nitromethane | HDPE |
| 54 | Ethylenediamine | HDPE |
| 55 | Glycerin | HDPE |

TABLE 8-continued

Identification number and liquid identifier
characterized in three container types

| Number | Liquid | Container |
|---|---|---|
| 56 | Mix 1 (C7) | HDPE |
| 57 | Mix 2 (B5) | HDPE |

Figure 20:
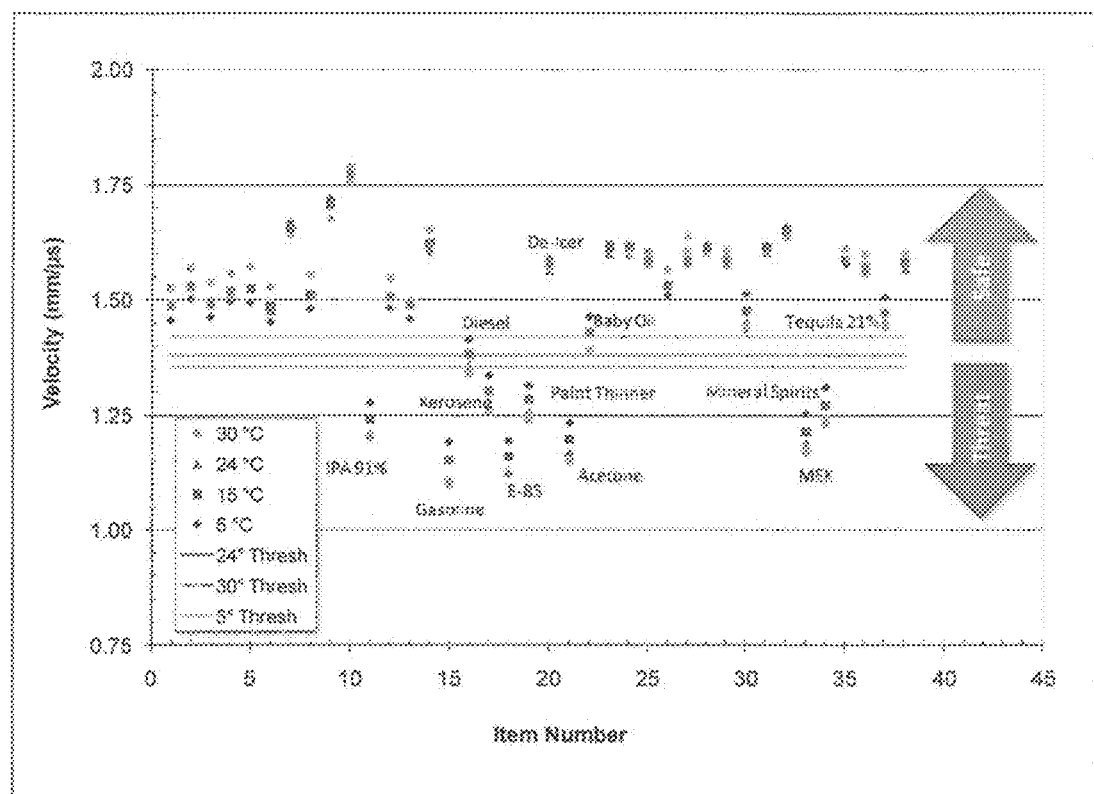
FIG. 20 illustrates an example a plot diagram for various liquids based on ultrasonic screening.
Figure 21:
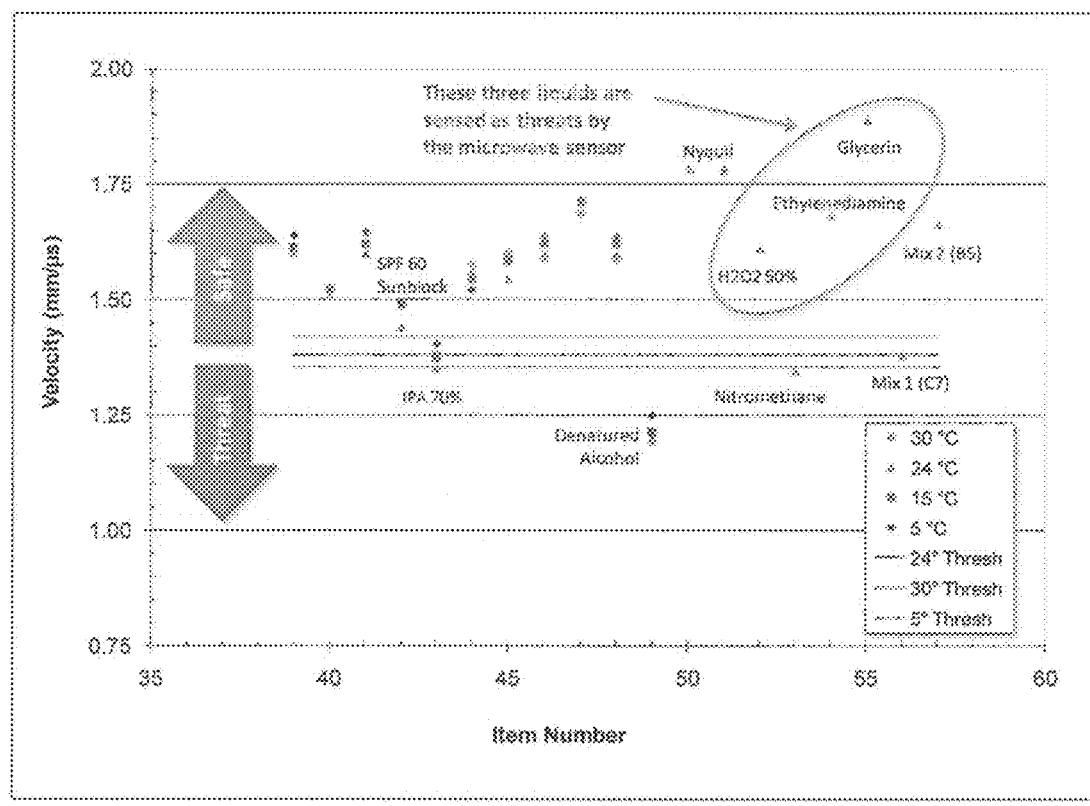
FIG. 21 illustrates an example a plot diagram for various liquids based on ultrasonic screening.

Preliminary measured ultrasonic results are presented in FIGS. 20 and 21. These two plots present a lot of data, so only threat liquids and liquids near thresholds may be identified specifically. In FIGS. 20 and 21, an acoustic velocity may be plotted for each liquid. Non-labeled liquids may be identified using Table 7 and Table 8. Most liquids may be characterized at the four temperatures indicated in the legends. Liquids illustrated in FIG. 21 that were plotted only at 24° C., may be liquids that were interrogated at Battelle Memorial Institute's (Battelle) explosives containment facility. These liquid were not heated nor cooled because of their potential to become unstable at these temperatures. Three distinct thresholds are plotted in FIGS. 20 and 21, corresponding to 5, 24 and 30° C. It is evident that both wave velocity and threshold may be functions of temperature. As large arrows in FIGS. 20 and 21 may indicate, liquids above a thresholds may be considered safe, and those below thresholds may be considered threats.

B. Metal Containers

Figure 22:
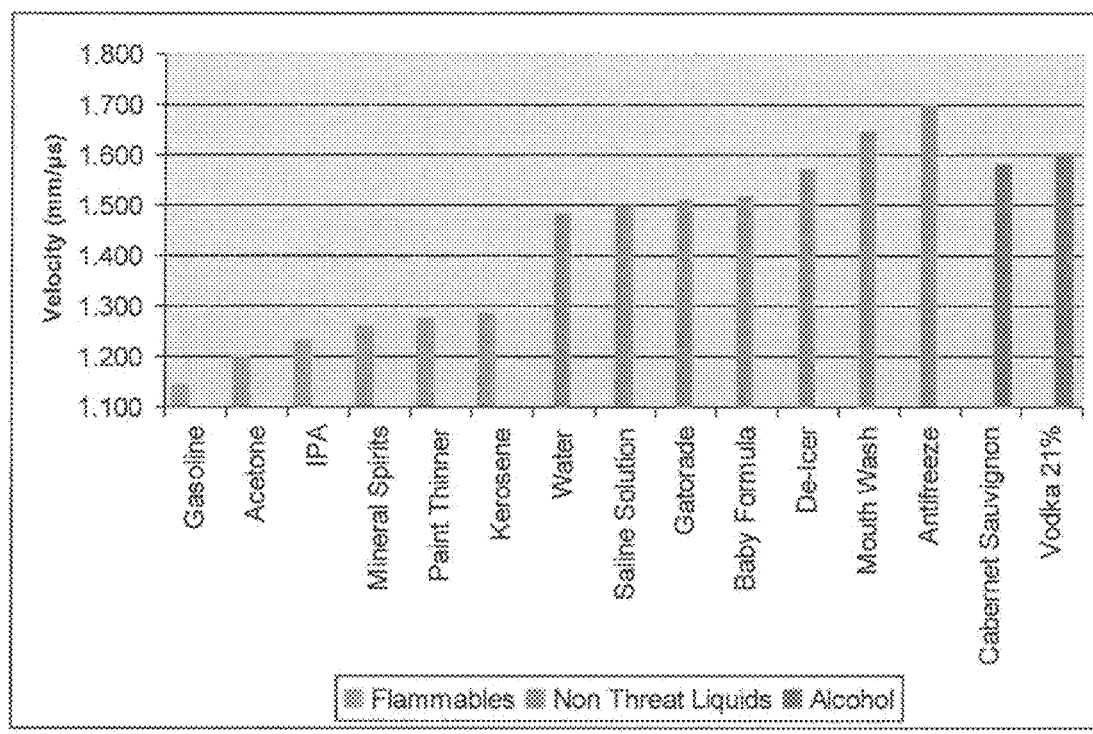
FIG. 22 illustrates example sensed ultrasonic velocities for a range of liquids.

Battelle characterized liquids in metal cans with an ultrasonic sensing system. FIG. 22 may provide an ultrasonic wave velocity, in mm/µs, for 15 liquids contained in soda cans of a same size and shape. It is evident that an acoustic sensor system may discriminate between threat liquids and non-threat liquids, as shown in FIG. 22.

Therefore, a screening system may exploit both radio frequency (RF) energy and ultrasonic energy to non-invasively determine whether or not a liquid contained in a sealed or unsealed container is hazardous or benign. A use of two independent measurement modalities (RF and ultrasonic) may have the capability to overcome problem deficiencies inherent to each modality when used alone. When a liquid is in a plastic or glass container, results of two measurements (i.e. RF and ultrasonic) may be combined to provide a more accurate screening response. In addition, an ultrasonic modality measurement capability may be capable of making a hazardous/benign liquid determination even when a container may be metal or metal coated. That is, as RF energy cannot penetrate metal containers, this modality alone may be unable to screen various containers often carried by the traveling public in airports and the like. Capabilities to respond to more threat liquids and gels contained in a wider variety of container geometries may exist, while also providing improved detection/false alarm statistics, and a user-friendly and cost-effective characterization platform suitable for use by transit and other such security personnel with minimal training.

Unless specifically stated to the contrary, the numerical parameters set forth in the specification, including the attached claims, are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and apparatuses have been illustrated by describing example embodiments, and while the example embodiments have been described and illustrated in considerable detail, it is not the intention of the applicants to restrict, or in any way limit, the scope of the appended claims to such detail. It is, of course, not possible to describe every conceivable combination of components or methodologies for purposes of describing the systems, methods, and apparatuses. With the benefit of this application, additional advantages and modifications will readily appear to those skilled in the art. Therefore, the invention, in its broader aspects, is not limited to the specific details and illustrative example and exemplary embodiments shown and described. Accordingly, departures may be made from such details without departing from the spirit or scope of the general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

As used in the specification and the claims, the singular forms "a," "an," and "the" include the plural. To the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. Finally, where the term "about" is used in conjunction with a number, it is intended to include ±10% of the number. In other words, "about 10" may mean from 9 to 11.

What is claimed:

1. An apparatus for detecting a presence of a container comprising a sample and determining a condition of the sample, comprising:

a holder for supporting the container comprising the sample;

a radio frequency (RF)transmitter configured to transmit an RF signal at the holder;

an RF receiver configured to receive a reflected RF signal of the RF signal;
and memory comprising data representative of a baseline reflected RF signal;
and a processor coupled to the memory and configured to:
transform the reflected RF signal into a frequency domain as a transformed reflected waveform;
transform the baseline reflected RF signal into the frequency domain as a transformed baseline waveform;
determine a ratio of the transformed reflected waveform to the transformed baseline waveform;
compare the ratio relative to a predetermined threshold to determine whether the container is being supported by the holder;
and evaluate the reflected RF signal relative to the baseline reflected RF signal to determine the condition of the sample wherein the condition is one of a hazardous condition or a non-hazardous condition.

2. The apparatus of claim 1, wherein air present at a location above the holder reflects the RF signal.

3. The apparatus of claim 2, wherein the processor is further configured to continuously monitor for the reflected RF signal waveform and evaluate the reflected RF signal to the baseline reflected RF signal.

4. The apparatus of claim 3, wherein to transform comprises conducting a discrete Fourier analysis on the baseline reflected RF signal and the reflected RF signal.

5. The apparatus of claim 1,
wherein the memory further comprises a database comprising data representative of a plurality of different RF signals associated with a respective hazardous sample; and
wherein the baseline RF signal is one of the plurality of different baseline RF signals.

6. The apparatus of claim 5, wherein to evaluate comprises:
comparing the reflected RF signal to the baseline RF signal to determine the condition of the sample in response to determining that the sample is being supported by the holder.

7. The apparatus of claim 5, wherein the sample is determined to be non-hazardous in response to the reflecting RF signal not matching any of the plurality of different RF signals.

8. The apparatus of claim 5, wherein the sample is determined to be hazardous in response to the reflecting RF signal matching one of the plurality of different hazardous substance RF signals.

9. A method for detecting a presence of a liquid in a screening system for analyzing liquid-filled containers, the method comprising:
transmitting, at a transmitter, a radio-frequency (RF) signal at a holder supporting the container comprising an unknown liquid;
monitoring, at a receiver, for a reflected RF signal of the RF signal;
retrieving, from memory, data representative of a baseline reflected RF signal;
conducting, at a processor, a discrete Fourier analysis on the baseline reflected RF signal to convert the baseline reflected RF signal to a transformed baseline waveform;
conducting, at the processor, the discrete Fourier analysis on the reflected RF signal to convert the reflected RF signal to a transformed reflected waveform;
calculating, at the processor, a ratio of the transformed reflected waveform to the transformed baseline reflected waveform;
comparing, at the processor, the ratio relative to a predetermined threshold to determine whether the container is being supported by the holder;
and evaluating, at the processor, the reflected RF signal relative to the baseline reflected RF signal to determine whether the liquid is one of is hazardous and non-hazardous in response to determining that the container is being supported by the holder.

10. A method for determining a condition of a liquid in a container comprising:
storing, at memory, data representative of a baseline reflected radio-frequency (RF) signal;
transmitting, at a transmitter, an RF signal at the container comprising a liquid;
receiving, at a receiver, a reflected RF signal in response to the transmitted RF signal reflecting off the liquid;
conducting, at a processor, a Fast Fourier Transformation (FFT) on the reflected RF signal to generate a signal transform;
conducting, at the processor, the FFT on the baseline reflected RF signal to generate a baseline transform;
determining, at the processor, a ratio of the signal transform to the baseline transform;
determining, at the processor, a difference between the signal transform and the baseline transform;
conducting, at the processor, a partial least squares regression analysis based on the ratio and the difference to generate a regression value for the liquid;
wherein the reflected RF-signal is received in at least one of a time domain for an RF time measurement and a frequency domain for an RF frequency measurement;
measuring, at a temperature sensor, a temperature of the liquid to compensate for changes in the RF radio signal and an ultrasonic velocity measurement of sound passing through the liquid caused by temperature;
calculating, at the processor, a signature for the liquid based on the regression value, the RF time measurement, the RF frequency measurement, the ultrasonic velocity, and the temperature;
and comparing, at the processor, the signature for the liquid to a database of signatures for liquids to determine a condition of the liquid, wherein the condition is one of a hazardous condition and a non-hazardous condition.

* * * * *